United States Patent [19]
Hültner et al.

[11] Patent Number: 5,164,317
[45] Date of Patent: Nov. 17, 1992

[54] METHOD FOR ENHANCED GROWTH AND PROLIFERATION OF MAST CELLS

[75] Inventors: Lothar Hültner, Munich; Jochen Moeller, Eichenau, both of Fed. Rep. of Germany; Catherine Uyttenhove, Gistoux; Jacques Van Snick, Kraainem, both of Belgium

[73] Assignee: Ludwig Institute for Cancer Research, Switzerland

[21] Appl. No.: 799,011

[22] Filed: Nov. 25, 1991

Related U.S. Application Data

[63] Continuation of Ser. No. 498,182, Mar. 23, 1990, abandoned.

[51] Int. Cl.$^5$ ............ C12N 5/00; C12N 5/02; C12P 21/02
[52] U.S. Cl. ............ 435/240.2; 435/240.21; 435/240.22; 435/240.24; 435/70.3
[58] Field of Search ............ 435/240.2, 240.21, 240.22, 435/240.24, 70.3

[56] References Cited

FOREIGN PATENT DOCUMENTS 287248 10/1988 Japan.

OTHER PUBLICATIONS

Moeller et al. (1989) J. Immunol. 142(10):3447–3451.
Hültner et al. (1989) J. Immunol 142(10):3440–3446.
Yang et al., Blood 74(6):1880–1884 (Nov. 1, 1989).
Moller et al., J. Immunol. 142(10):3440–3446 (May 15, 1989).

Primary Examiner—David L. Lacey
Assistant Examiner—Gian P. Wang

[57] ABSTRACT

The glycoprotein known as P40, characterized by a molecular weight of from about 30 to 40 kilodaltons and an isoelectric point of about 10, previously recognized as a helper T cell growth factor, also enhances growth and proliferation of mast cells and their maintenance viability and differentation status in vitro.

8 Claims, 3 Drawing Sheets

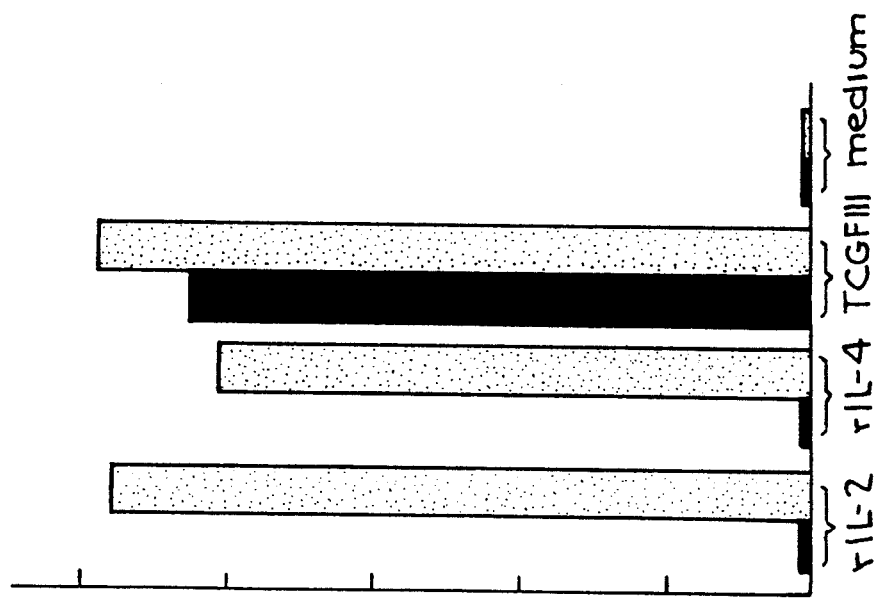
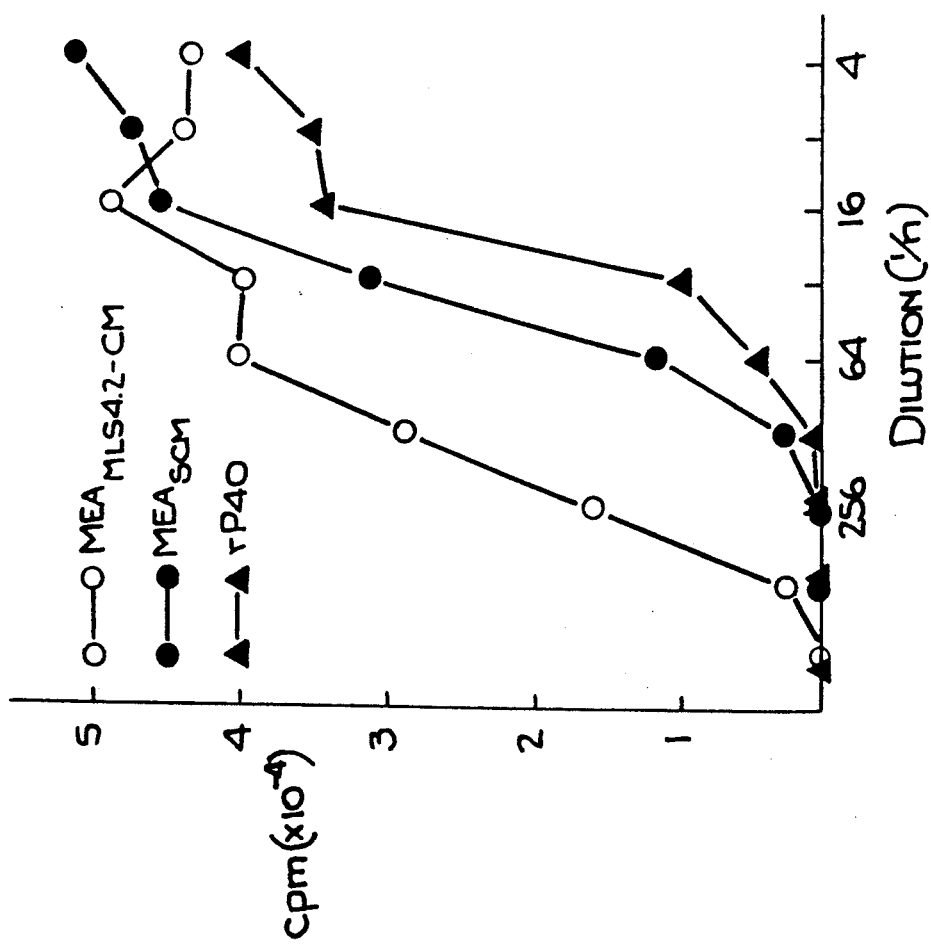

METHOD FOR ENHANCED GROWTH AND PROLIFERATION OF MAST CELLS

This application is a continuation, of application Ser. No. 498,182, filed Mar. 23, 1990, now abandoned.

FIELD OF THE INVENTION

This invention relates to a method for enhancing cell growth or proliferation, using a naturally occurring growth factor. More specifically, it relates to a method for stimulating the growth or proliferation of mast cells, especially bone marrow mast cells ("BMMC" hereafter).

RELATED APPLICATIONS

Attention is drawn to U.S. patent application Ser. No. 07/246,482, filed Sep. 19, 1988 to Van Snick, et al., and entitled "T Cell Growth Factor". This application, the disclosure of which is incorporated by reference, describes a glycoprotein characterized as a T cell growth factor, referred to as "P40". This growth factor is a glycoprotein, having a molecular weight in a range of from about 30 to about 40 kilodaltons, and an isoelectric point ("pI") of about 10.

BACKGROUND AND PRIOR ART

The field of cell biology has seen an enormous expansion in the area of "growth factors" or other protein and glycoproteins which influence the manner and degree to which cells react to various stimuli. One family of these (glyco)proteins, known as the cytokines, either directly or indirectly mediates host cell defense mechanisms or tissue growth differentiation. Among the materials so identified are the interferon family (INF-$\alpha$, INF-$\beta$, and INF-$\gamma$, transforming growth factor (TGF), tumor necrosis factor (TNF), the various colony stimulating factors such as "M-CSF" or "macrophage colony stimulating factor", "G-CSF" or "granulocyte colony stimulating factor", and "GM-CSF" or "granulocyte macrophage, colony stimulating factor". A growing family includes the "interleukins", which are generally referred to as "IL-X", where "X" is a whole number. This application concerns a new interleukin, referred to hereafter as "IL-9".

The literature on these proteins and glycoproteins, be it patent, technical or popular, is vast. Exemplary of the patent literature in this field are U.S. Pat. Nos. 4,851,512 (IL-2 derivatives), 4,863,727 (therapeutic use of IL-2 in combination with TNF), and U.S. Pat. Nos. 4,774,320; 4,772,685; 4,762,914; 4,681,844, and 4,404,280, all of which relate to some degree to IL-1. Also of interest are U.S. Pat. Nos. 4,810,643 and 4,833,127, relating to G-CSF, and U.S. Pat. Nos. 4,676,983, 4,530,784, and 4,431,582, relating to various cell growth and contact factors. Examples of the popular literature in the field include Smith, "Interleukin-2" in Scientific American 262(3): 50–57 (March, 1990), and Old, "Tumor Necrosis Factor" in Scientific American 258(5): 59–75 (May, 1988).

The above identified patent application, i.e., Ser. No. 07/246,582, to Van Snick et al., the disclosure of which is incorporated by reference, taught the discovery of a T cell growth factor which was produced by helper T cells, having a molecular weight of from about 30 to 40 kilodaltons and an isoelectric point of about 10. This factor would cause T cells, such as helper T cells, to proliferate when the factor was incubated with the T cells. The proliferation and growth of the T cells was IL-2 and IL-4 independent, and was also independent of antigen presence. As described therein the "P40" as it was called, was purified from the supernatant of lectin stimulated mouse helper T cells. The amino acid sequence of the protein and the DNA sequence expressing it were also described.

In a subsequent, continuation in part application, i.e., Ser. No. 07/408,155, filed Sep. 15, 1989, the disclosure of which is incorporated by reference, and in a further continuation in part, i.e., Ser. No. 07/462,158 filed Jan. 8, 1990, the disclosure of which is incorporated by reference, additional data on P40 were presented. This additional data include information on the human protein and the DNA sequence expressing the human protein. Additionally, these data can be reviewed in, e.g., Uyttenhove, et al., Proc. Natl. Acad. Sci. USA 85: 6934 (1988); Van Snick, et al., J. Exp. Med. 169: 363 (1989); Yang, et al., Blood 74: 1880 (1989). The disclosures of these last three papers are all also incorporated by reference herein. Additional data, as described by Schmitt, et al., Eur. J. Immunol. 19: 2167–2170(1989), show that P40 is apparently identical to "T cell Growth Factor III" ("TCGF III"), and is not a general T cell growth factor. The Schmitt paper is also incorporated by reference herein.

An additional factor of interest has been referred to in the literature as having "Mast Cell Growth Enhancing Activity". This factor was derived from pokeweed mitogen stimulated mouse spleen cell conditioned medium. This factor, and a partial purification thereof, are described in Hültner, et al., J. Immunol. 142: 3440–3446 (May 15, 1989), and Moeller, et al., J. Immunol. 142: 3447–3451 (May 15, 1989). Both of these disclosures are also incorporated by reference.

The Moeller paper, as attested to by its title, described partial purification of the factor, referred to as MEA hereafter. The partially purified material, which showed mast cell growth enhancing activity, was characterized by a molecular weight of from about 37 to about 43 kilodaltons, and an isoelectric point of from 6.2 to 7.3. The partially purified material was found to stimulate bone marrow mast cells, and, in the presence of IL-3, acted synergistically with respect to the proliferating effect on bone marrow mast cells. It was later found that the partially purified material could also sustain proliferation of a murine IL-3 dependent mast cell line in the absence of both IL-3 and IL-4. See, Hultner, et al., Exp. Hematol. 17: 1578 (1989), the disclosure of which is incorporated by reference.

Upon purification to homogeneity, it was found, unexpectedly, that MEA is identical to the factor previously reported as P40. It has also been found, surprisingly, that P40 has the same proliferative effect on mast cells as does MEA. The similarity of properties, characteristic of the interleukin cytokines, suggests that the materials be referred to as interleukin-9 ("IL-9" hereafter), and the invention relates to a method for enhancing the growth or proliferation of mast cells using the purified material, i.e., the "IL-9". For convenience hereafter, the IL-9 will be referred to in terms of its molecular weight and isoelectric point characteristics, i.e., a molecular weight of from about 30 to 40 kilodaltons, and an isoelectric point of about 10. Unless stated to the contrary, reference to "MEA" means MEA purified to homogeneity.

BRIEF DESCRIPTION OF THE FIGURES

FIGS. 1A and 1B depict studies showing the effect of purified MEA on the proliferation of TCGF III/P40 responsive T cells (FIG. 1A), as compared to control cultures, which were stimulated with one of recombinant IL-2, recombinant IL-4, TCGF III, or medium containing antisera to IL-2 and IL-4, or lacking it (FIG. 1B).

DETAILED DESCRIPTION OF PREFERRED EMBODIMENTS

Example 1

Figure 2B:
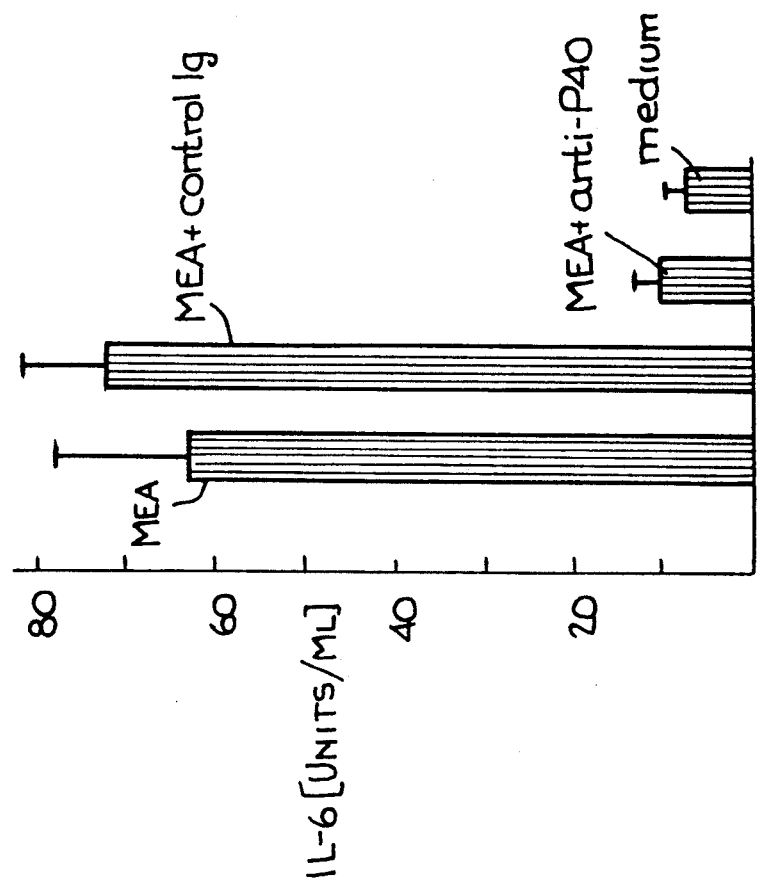
FIG. 2A and FIG. 2B also show that antisera to P40 also blocks the effect of purified MEA in mast cell cultures, comparing stimulation with MEA alone or in mixture with anti-P40 antibodies or control IgG at different concentrations of the various materials.

This example describes the preparation of the protein materials used in the later experiments. Partially purified MEA, from spleen cell conditioned medium, was obtained following Moeller, et al., J. Immunol. 142: 3447-3450 (1989), previously incorporated by reference. Briefly, serum free spleen cell conditioned medium (SCM), was prepared following Hültner, et al., J. Immunol. 142: 3440-3446 (1989), incorporated by reference herein. This was concentrated eightfold on YM10 Amicon ultrafiltration medium. The resulting, concentrated SCM was purified on cation exchange chromotography columns, using S-Sepharose. Following this, the resulting partially purified material was concentrated over an Amicon YM10 ultrafiltration membrane, followed by purification on a Procion Red containing column. The resulting fraction was then subjected to affinity chromatography on Con A-Sepharose. This was followed, either with SDS-gel separation, or via use of IEF to obtain a partially purified MEA.

MEA purified to homogeneity as used herein is described in Moeller, et al., J. Immunol. 144(11); 4231-4234 (1990), the disclosure of which is incorporated by reference. For convenience, however, the major features of the protocol are described herein.

As described by Moeller, et al., J. Immunol. 142: 3447-3450 (1989), both cation exchange and Procion Red affinity chromatography were used to separate MEA from IL-4 (cation exchange), and IL-3 (procion red), in the supernatant of MLS-4.2 CM. The IEF separation using lyophilized product of procion red chromatography was then followed, as per Moeller, et al., supra.

Fractions 10-15 of the IEF filtration were then pooled, and subjected to HPLC gel filtration. This involved pooling the fractions, followed by concentration in a dialysis bag with 20% polyethylene glycol (PEG 20,000) in a gel filtration buffer which had a final volume of about 500 μl. This was applied, in 100 μl portions, to a tSK G 2000 SW column (7×600 nm), using a flow rate of 0.5 ml/min and a fraction size of 1 ml. This yielded a single peak of MEA, having a molecular weight of about 39 kilodaltons. This material had a biologic activity of $6.72 \times 10^6$ μ/mg. This total recovery was about 11%, and was 0.22 mg compared to a starting total protein of 2280 mg in the conditioned medium of the Mls-4.2-CM cell line.

Mouse P40 cDNA clone P40.2B4 described by Van Snick, et al., J. Exp. Med. 169: 363-368 (1989) was subcloned into the BamH I site of the baculovirus expression vector pVL941. This cDNA has nucleic acid sequence:

```
5' CAGACTCCCGTCAACATGTTGGTGACATACATCCTTGCCTCTGTTTTGCTCTTCAGTTCT

GTGCTGGGCCAGAGATGCAGCACCACATGGGGCATCAGAGACACCAATTACCTTATTGAA
                     100

AATCTGAAGGATGATCCACCGTCAAAATGCAGCTGCAGCGGCAACGTGACCAGCTGCTTG

TGTCTCTCCGTCCCAACTGATGATTGTACCACACCGTGCTACAGGGAGGGACTGTTACAG
                                      200

CTGACCAATGCCACACAGAAATCAAGACTCTTGCCTGTTTTCCATCGGGTGAAAAGGATA
                                                              300

GTTGAAGTCCTAAAGAACATCACGTGTCCGTCCTTTTCCTGCGAAAAGCCATGCAACCAG

ACCATGGCAGGCAACACACTGTCATTTCTGAAGAGTCTCCTGGGGACGTTCCAGAAGACA
                     400

GAGATGCAAAGGCAGAAAAGCCGACCATGAAGACAGATGCTATTTATTCTATTTATTGAA

TTTACAAAACCTCCCCTCCTTAACTGTTACAGTGAAGAAATAAACTAAGCTATTCT 3'
                     500
```

Recombinant baculovirus expressing the P40 protein was isolated by described techniques and used to infect Sf9 cells that were grown in a 4:1 mix of IPL-41 (JR Scientific) and TC100 (Gibco) media supplemented with 10% FBS. The purification of recombinant P40 (rP40) was carried out in four sequential steps and monitored in TS1 assays. Medium from infected Sf9 cells, diluted 5-fold with $H_2O$ and adjusted to pH 5.2 by addition of 20 mM sodium acetate, was adsorbed on sulfopropyl Sephadex beads.

After washing with 20 mM NaCl and 50 mM sodium acetate pH 5, rP40 was eluted from the gel with 0.9M NaCl, $10^{-4}$ v/v Tween-20 and 0.1M Tris-HCl pH 8. The eluted material was fractionated by gel filtration on a AcA54 column followed by an FPLC sulfopropyl cation-exchanger equilibrated at pH 7 with 50 mM sodium phosphate. Under these conditions, rP40 represented approximately 80% of the material binding to the column. Final purification was achieved by HPLC chromatography on a Vydac C4 column equilibrated in 0.05% trifluoroacetic acid and eluted with a gradient of acetonitrile. The purified protein had a Mr of 22-25 kDa in SDS-PAGE. Following this, the rP40 was radiolabelled with $^{125}$I by a two-step procedure. Radioactive NaI (1fmCi in 50 ul of 0.1M sodium phosphate buffer pH 7.5) was first incubated for 1 min at 4° C. in a polypropylene tube coated with iodogen (Pierce). The radioactive material was then transferred to a tube containing 1-2 ug of rP40 in the same buffer. After 5 minutes, the reaction was quenched by adding excess unlabeled NaI. The iodinated protein was separated from free iodide by adsorption on sulfopropyl-Sephadex beads. The eluted material had a specific activity of 1-2000 cpm/1 mole. The purity of the radiolabeled protein was verified by SDS-PAGE.

Additional proteins used in the following examples, including recombinant IL-3 and IL-4 ("rIL-3, rIL-4"), antibodies, were either purchased or donated by different investigators. Anti IL-2 and IL-4 antibodies were prepared following Mosmann, et al., J. Immunol. 136: 2348 (1986), using donated cell line 54N6.1, or following Ohara, et al., Nature 315: 333 (1985), using donated cell line 11B11. Rabbit antiserum against native, homogeneous P40 was prepared following Uyttenhove, et al., Proc. Natl. Acad. Sci. USA 85: 6934 (1988).

Example 2

This example describes the cell lines used in experiments which follow.

Hültner, et al., Immunology 67: 408 (1989), describe a method for generating a homogeneous population of murine BMMC in a limiting dilution microculture system, and this protocol was followed to culture BMMC. In addition, cell line L 138.8A, which is a factor dependent, IL-3/IL-4/MEA responsive BMMC cell line described by Hultner, et al., supra, TS1, which is a P40 responsive murine T cell line, described by Uyttenhove, et al., supra, ST2/k9.4a 2, which is a TCGFIII-responsive CD4+ T cell clone described by Schmitt, et al., Eur. J. Immunol 19(11):2167-2170 (1989), MLS 4.2, which is a murine IL-2 dependent Mls$^a$-specific T cell line which produces MEA and TCGF III on activation, also described by Schmitt, et al., supra, TUC7.51, which is a P40-producing helper T cell line, taught by Uyttenhove, et al., supra, and 7TD1, an IL-6-dependent mouse hybridoma cell line, described by Van Snick, et al., Proc. Natl. Acad. Sci. USA 83: 9679 (1986), were the cell lines used.

Example 3

The effect of MEA on TCGF/P40 responsive T cells was studied. In these experiments, cell line ST2/K9.4a2, at a concentration of $2.5 \times 10^3$/well, at 100 ul of culture per well, was stimulated with serial dilutions of one of recombinant P40 (stock: 1 ng/ml), partially purified MEA (stock: 10 μ/ml), or highly purified MEA (stock: 25 μ/ml). The stimulation was for 48 hours. Stimulation, should it lead to proliferation, could be measured via measuring incorporation of $^3$H thymidine by the cells. This was added over the last 18 hours of stimulation, at 0.1 μCi/well.

FIG. 1A shows parallel incorporation of the radioactive thymidine over the dilutions, indicating a similar effect of the MEA and P40 in the cells.

In control cultures, the cells were stimulated with one of rIL-2, rIL-4, or TCGF III, with or without anti IL-2 or anti IL-4 antisera. Presence of the antisera is indicated by the dark bar, absence by the pied bar.

Example 4

Experiments were performed to determine the effect of antisera against P40 on the effect of MEA on mast cell cultures (cell line L138.8A).

In these experiments, triplicate cultures of the cells ($1.5 \times 10^4$ ml, 100 μl/well) were stimulated with serial dilutions of the highly purified MEA (stock: 50 μ/ml), either alone, or together with one of anti-P40 antibodies or control IgG. In either case, the amount was constant (10 μg/ml).

Figure 2A:
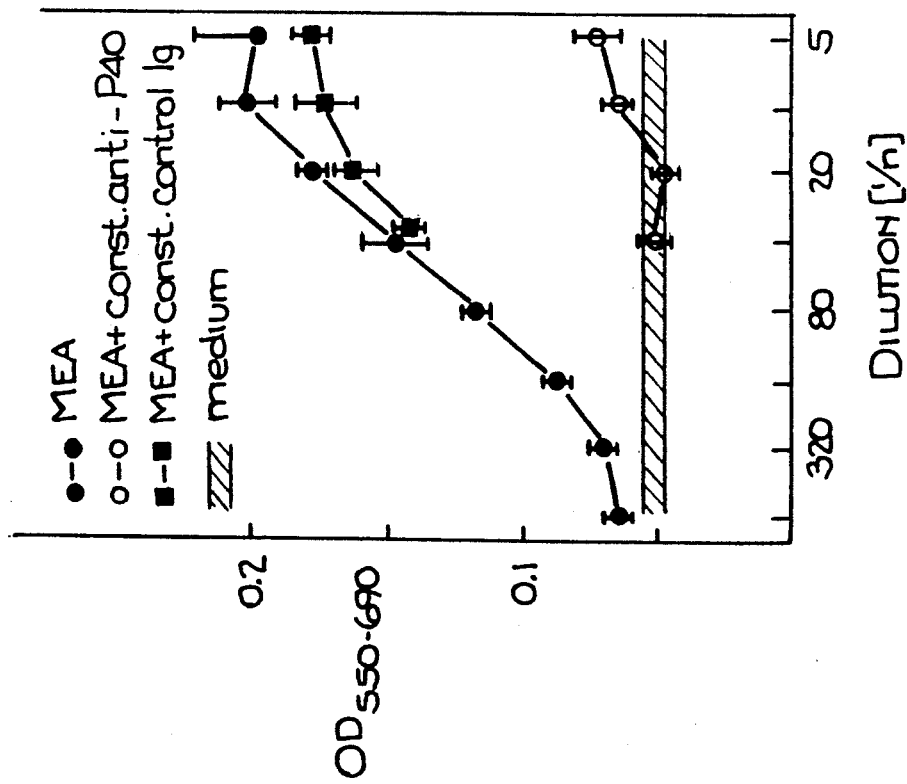

In FIG. 2A it is shown that the anti P40 antibody almost completely inactivated the effect of the MEA, as compared to the controls.

A second set of data was generated in which cultures of L138.8A cells ($2 \times 10^5$/ml) were stimulated with 20 μ/ml of MEA, either alone, with anti P40 antibodies, or control IgG (10 μg/ml each). Supernatants of the cultures were tested for IL-6 production. FIG. 2B shows the mean values ± standard deviation.

The effect of the anti-P40 antibodies on the effect of MEA is evidenced by the dramatic drop therein.

In experiments not described herein, IL-3/IL-4 induced proliferation of the cells, and IL-3/IL-4 stimulated IL-6 production were not affected by the anti-P40 antibodies.

Example 5

The effect of P40 on MEA sensitive mast cells, as exemplified by cell line L138.8A was studied.

Microcultures (100 μl/ml) of L138.8A cells ($1.5 \times 10^4$/ml) were stimulated with serial dilutions of purified growth factors at 1:5 dilutions, corresponding to 20 ng/ml of recombinant P40, 50 μ/ml MEA, and 40 μ/ml of IL-3. In addition, MEA and recombinant P40 were tested in the presence of saturating amounts of IL-3, i.e., 20 μ/ml. A depiction of growth curves, which shows the effect of the molecules on the proliferation of the cell line, is presented in FIG. 3. The data were obtained by performing an MTT assay. This is a colorimetric assay, as described by Mosmann, J. Immunol. Meth. 65: 55 (1983), and Hültner, et al., J. Immunol. 142: 3440-3445 (1989).

Figure 3:
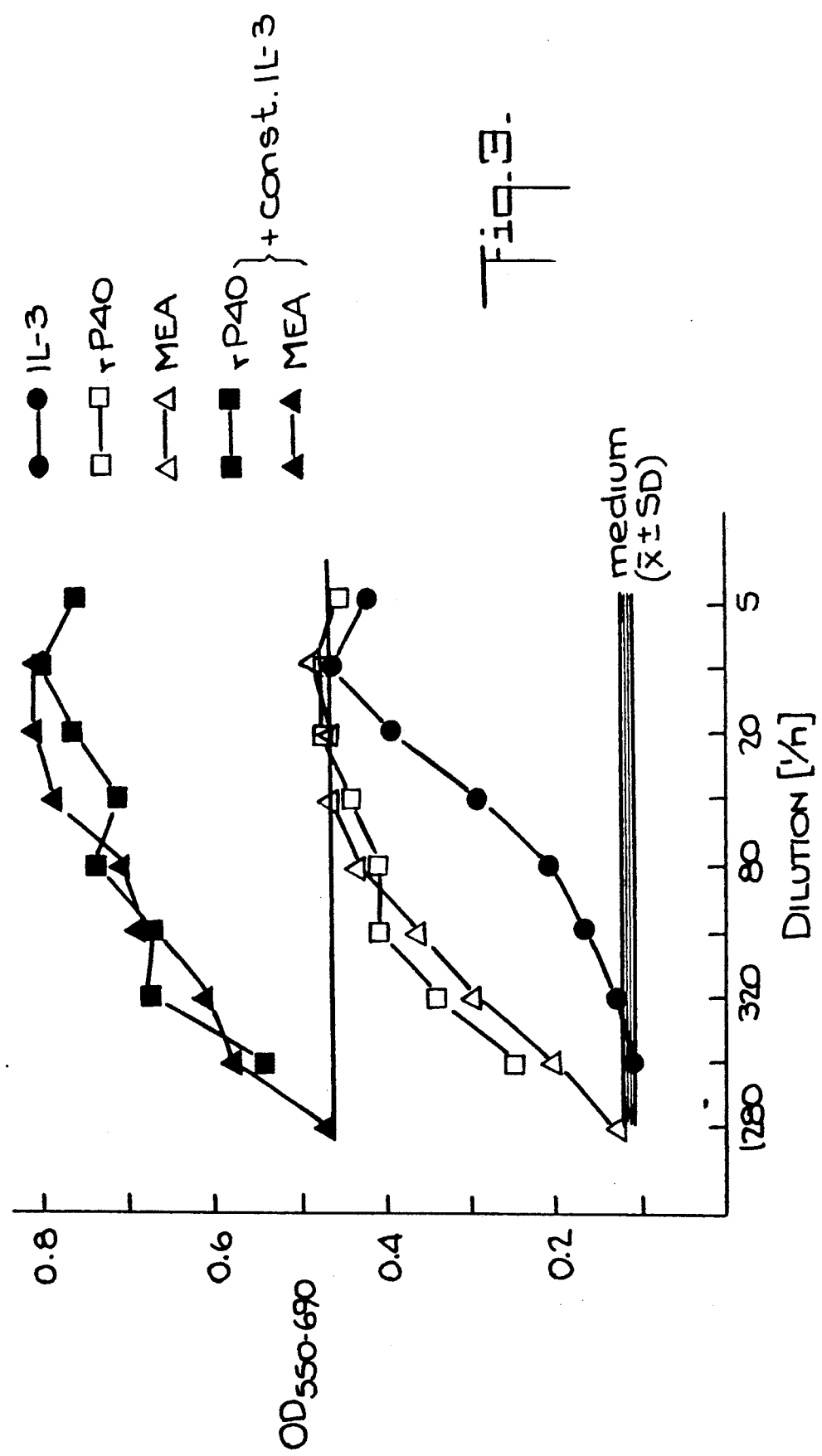
FIG. 3 depicts the proliferative effect of recombinant P40 on MEA sensitive mast cells.

The data in FIG. 3 show comparable results for rP40 and MEA, either alone or in combination with IL-3.

Example 6

The effect of various factors on the stimulation of IL-6 production on mast cells, exemplified by L138.8A, was investigated.

In these experiments, duplicate 24 well plate cultures (0.5 ml/well) of L138.8A mast cells ($2 \times 10^5$/ml) were stimulated with one of rP40, MEA, rIL-3, rIL-4, or control medium, for 24 hours. Following the stimulation, the IL-6 activity in the well supernatants was measured, using dose response curves obtained using an IL-6 assay using hybridoma cells of 7TD1, which is described supra. While various concentrations were used, the following data only show the results obtained using the saturating maximum dose.

TABLE 1

| FACTOR & DOSE | IL-6 activity (μ/ml) |
| --- | --- |
| rP40 (20 ng/ml) | 66.8 ± 1.7 |
| MEA (40 μ/ml) | 64.9 ± 11.0 |
| rIL-3 (100 μ/ml) | 14.5 ± 2.7 |
| rIL-4 (400 μ/ml) | 20.8 ± 2.8 |

TABLE 1-continued

| FACTOR & DOSE | IL-6 activity (μ/ml) |
|---|---|
| Medium | 6.1 ± 1.4 |

IL-6 activity is presented as values ± standard deviations.

These data show that rP40 significantly stimulated the factor dependent mast cells.

Example 7

The following experiment describes the proof of a specific binding site for P40, using a factor dependent, and an autonomous BMMC cell line.

Various cell types described in Example 2 (TS1.C3, a P40 dependent cell line; L138.8A, a factor dependent mast cell line; L138.C, an autonomous cell line; 2 week old BMMCs, and, as a control, MethA, a fibrosarcoma cell line) were incubated for three hours at 4° C. with radioiodinated rP40 (0.5 nm), in the presence or absence of a 100 fold excess of unlabeled rP40.

In order to label the rP40, it was iodinated in a two step process, in which iodogen coated tubes were used to oxidize $Na^{125}I$. The oxidized material was then transferred to a solution the rP40. Specific activities of 100,000 cpm/ng were regularly achieved in this way, without any significant decrease in the protein's activity.

Specific binding sites for P40 were demonstrated via the data shown in Table 2. Cells were incubated for 3 hours at 4° C. with radio-iodinated rP40 (0.5 nM) in the presence or absence of a 100-fold excess of unlabeled rP40. The radioactivity measured in the presence of excess cold P40 was subtracted to calculate specific binding. MEA activity was measured in the TS1 assay.

| Cells | MEA (U/ml) | Specific Binding (molecules/cell) |
|---|---|---|
| TS1.C3, P40 dependent T cells | — | 4109 |
| | 8000 | 214 |
| | 2000 | 605 |
| | 500 | 1818 |
| | 125 | 2040 |
| | 31 | 3776 |
| L138.8A, factor-dependent mast cell line | — | 2208 |
| L138.C, autonomous mast cell line | — | 331 |
| BMMC 2 wk-old | — | 128 |
| MethA, fibrosarcoma | — | 10 |

These results not only show the existence of a P40 receptor on MEA sensitive mast cell such as TS1.C3, but also show that there is competition between the two proteins MEA and P40 for those sites.

The next samples are copied from Uyttenhove et al., supra, which has been incorporated by reference:

EXAMPLE 8

Cell line TUC 2.15 is a C57BL/6 helper T cell line that requires antigen and antigen presenting cells for long term growth in vitro. In an attempt to grow these cells without feeders and antigens, culture medium (Dulbecco's modified Eagle's medium supplemented with 10% Fetal bovine serum, 50 μM 2-mercaptoethanol, 0.55 mM L-arginine, 0.24 mM L-asparagine and 1.25 mM L-glutamine), was supplemented with 10% of autologous supernatant obtained after stimulation with Con A (5 ug/ml). The autologous supernatant had been obtained from cultures stimulated 2 weeks prior to collection with antigen and feeder cells. The T cells from which the supernatant was obtained were adjusted to $2 \times 10^6$ cells/ml, and were incubated for 2-3 days with a medium containing 0.5% fetal calf serum and the Con A. The supernatant was obtained via centrifugation (10,000×g, 20 minutes).

The supernatant was found to induce cell proliferation of TUC 2.15 without need for further feeder cells or antigen. This activity was not inhibited by anti IL-2 or anti IL-4 receptor antibodies, indicating that these did not mediate the proliferation.

Example 9

The supernatant described in Example 8 readily stimulated development of permanent antigen independent cell lines, which could be maintained by subcultivation every 3-4 days in medium supplemented with 1% supernatant. This was the case with TUC 2.15, noted supra, and TUC 7.51. Supernatant from either cell line supported the other.

A cell line, referred to as TS1, was derived from the foregoing experiments on TUC 2.15. Cell line TS1 had a doubling time of 11 hours, and responded of very small concentration of supernatant half-maximal proliferation occurring at dilutions between $1:10^5$ and $1:10^4$ (v/v).

Example 10

Using Con A to stimulate TUC 2.15 and TUC 7.51, large amounts of supernatant were produced. This was concentrated by absorption of silicic acid and applied to an Ultrogel AcA 54 gel filtration column (LKB). Major growth promoting activity eluted as a symmetrical peak in the 30-40 kilodalton region, and was described by trypsin. It had a pI of about 10, was glycosylated, and retained 60% activity on a lentil lectin column.

Example 11

The material obtained in Example 10, referred to as P40, was subjected to further separation of a TSK-phenyl column, followed by passage through a Mono-Q anion exchange column equilibrated at pH 9.5. At this pH, contaminants mostly remained, but due to P40's high pI, it eluted mainly in the flowthrough. The purified protein showed molecular mass of 32-39 kdal in NaDodSO4/PAGE.

Example 12

This example describes the TS1 assay. The derivation of cell line TS1 was given supra. In growth factor assays, TS1 cells were washed free of supernatant of $3 \times 10^3$ cells per well in 200 μl, using serial dilutions of tested samples. After 3 days, cell growth was measured by colorimetric determination of hexosaminadase following Landegren, J. Immunol. Meth 67: 379-388 (1984). Dilutions giving half maximal absrbance at 405 nm was assigned 1 unit of activity per ml, arbitrarily.

The data presented supra shows that purified MEA ("biologically pure" MEA) and P40 behave almost identically with respect to their biological properties. Specifically, both support growth of MEA sensitive mast cells, in particular, bone marrow mast cells. They both also induce IL-6 secretion. In experiments not elaborated upon herein, P40 also extended the survival of mast cells in primary culture.

It was also found that highly purified MEA stimulated growth and proliferation of P40 dependent cell lines. Antisera directed against P40 also inhibited the action of MEA on the mast cells. Specific binding sites for P40 were found on mast cells, and, coupled with competition with P40 for binding to P40 dependent T cells, this leads to the conclusion that the molecules are identical. In so concluding, the range of properties for each molecule is extended, and suggest that the molecule be designated as an interleukin, i.e., IL-9.

The finding that IL-9 stimulates proliferation and growth of mast cells suggests application to allergy therapy. It is known that proliferation of mast cells is a key part of an allergic reaction, and is responsible, at least in part, for the physiological manifestations of the response. Treating an affected individual with an IL-9 antagonist, either before expected exposure to an allergen, or after the initiation of a response, should mediate the degree of proliferation, and hence the accompanying physiologic symptoms.

The interleukin can also be used in connection with therapy of individuals who have pathological conditions characterized by abhorrent mast cell activity, such as abhorrent growth or function. In such situations, IL-9 administered in an effective amount, would be expected to rectify such conditions.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for enhancing proliferation of mast cells comprising contacting said mast cells with an amount of purified interleukin-9 characterized by a molecular weight of from 30 to 40 kilodaltons and an isoelectric point of 10 sufficient to enhance proliferation of said mast cells.

2. Method of claim 1, wherein said mast cells are bone marrow mast cells.

3. Method of claim 1, further comprising contacting said mast cells with purified interleukin-3.

4. Method of claim 1, wherein said purified interleukin-9 is obtained from murine spleen cells.

5. Method of claim 1, wherein said purified interleukin-9 is obtained from T cells.

6. Method of claim 1, wherein said purified interleukin-9 is produced via recombinant DNA.

7. Method of claim 1, wherein said purified interleukin-9 is administered to a subject having a pathological condition characterized by aberrant mast cell growth or function.

8. Method for enhancing proliferation of mast cells comprising contacting said mast cells with an amount of purified recombinant, interleukin-9, characterized by a molecular weight of from 22-25 kilodaltons as determined by SDS-PAGE sufficient to enhance proliferation of mast cells.

* * * * *